United States Patent
Macias et al.

(10) Patent No.: US 10,973,868 B2
(45) Date of Patent: Apr. 13, 2021

(54) COMPOSITION FOR TOPICAL USE BASED ON A CARNOSINE-MAGNESIUM COMPLEX

(71) Applicant: Outplay Inc., Victoria (CA)

(72) Inventors: Chad Macias, San Diego, CA (US); Tim Sharpe, Portland, OR (US); Massimo Ferrari, Copiano (IT)

(73) Assignee: Outplay, Inc.

( * ) Notice: Subject to any disclaimer, the term of this patent is extended or adjusted under 35 U.S.C. 154(b) by 0 days.

(21) Appl. No.: 16/077,794

(22) PCT Filed: Feb. 17, 2017

(86) PCT No.: PCT/IB2017/050907
§ 371 (c)(1),
(2) Date: Aug. 14, 2018

(87) PCT Pub. No.: WO2017/145030
PCT Pub. Date: Aug. 31, 2017

(65) Prior Publication Data
US 2019/0216880 A1    Jul. 18, 2019

Related U.S. Application Data

(60) Provisional application No. 62/383,528, filed on Sep. 5, 2016.

(30) Foreign Application Priority Data

Feb. 22, 2016 (WO) .................. PCT/IB2016/050927

(51) Int. Cl.

| | | |
|---|---|---|
| A61K 38/05 | (2006.01) | |
| A61K 47/10 | (2017.01) | |
| A61K 47/14 | (2017.01) | |
| A61K 47/22 | (2006.01) | |
| A61P 21/00 | (2006.01) | |
| A61K 9/00 | (2006.01) | |
| A61P 25/28 | (2006.01) | |
| A61P 19/02 | (2006.01) | |
| A61P 35/00 | (2006.01) | |
| A61P 9/00 | (2006.01) | |
| A61P 3/10 | (2006.01) | |
| A61Q 19/00 | (2006.01) | |
| A61K 9/06 | (2006.01) | |
| A61K 8/49 | (2006.01) | |
| A61K 8/19 | (2006.01) | |
| A61K 31/4164 | (2006.01) | |
| A61K 8/04 | (2006.01) | |
| A61K 33/06 | (2006.01) | |
| A61K 47/02 | (2006.01) | |
| A61K 47/38 | (2006.01) | |
| A61K 47/44 | (2017.01) | |

(52) U.S. Cl.
CPC ................ *A61K 38/05* (2013.01); *A61K 8/04* (2013.01); *A61K 8/19* (2013.01); *A61K 8/49* (2013.01); *A61K 9/0014* (2013.01); *A61K 9/06* (2013.01); *A61K 31/4164* (2013.01); *A61K 33/06* (2013.01); *A61K 47/10* (2013.01); *A61K 47/14* (2013.01); *A61K 47/22* (2013.01); *A61P 3/10* (2018.01); *A61P 9/00* (2018.01); *A61P 19/02* (2018.01); *A61P 21/00* (2018.01); *A61P 25/28* (2018.01); *A61P 35/00* (2018.01); *A61Q 19/00* (2013.01); *A61K 47/02* (2013.01); *A61K 47/38* (2013.01); *A61K 47/44* (2013.01)

(58) Field of Classification Search
None
See application file for complete search history.

(56) References Cited

U.S. PATENT DOCUMENTS

2015/0147360 A1* 5/2015 Levy ...................... A61Q 19/08
424/401
2015/0342854 A1* 12/2015 Shibuya ................. A61Q 19/08
424/62

FOREIGN PATENT DOCUMENTS

| JP | H04-178314 A | 6/1992 |
|---|---|---|
| WO | 02/26940 A1 | 4/2002 |
| WO | 2015-026954 A1 | 2/2015 |

OTHER PUBLICATIONS

Sale et al. (Amino Acids (2013) 44:1477-1491.*

* cited by examiner

*Primary Examiner* — Patricia Duffy
*Assistant Examiner* — Garen Gotfredson
(74) *Attorney, Agent, or Firm* — Lorraine Hernandez; Kegler, Brown, Hill & Ritter Co., LPA.

(57) ABSTRACT

The present disclosure relates to a composition comprising a carnosine-magnesium complex. The composition is designed to be applied to the skin and causes an increase in carnosine levels in the body. The topical 5 composition comprising a carnosine-magnesium complex has the effect of improving an athlete's physical performance and may be effective for the treatment of a variety of medical conditions. Also disclosed is a method for preparing the carnosine-magnesium complex.

9 Claims, No Drawings

COMPOSITION FOR TOPICAL USE BASED ON A CARNOSINE-MAGNESIUM COMPLEX

TECHNICAL FIELD

The present disclosure relates to compositions for topical use, such as gel-cream products, particularly to a topical transdermal composition and method for delivering nutrients and/or other substances through the skin. Specifically, the present disclosure relates to a carnosine-magnesium complex for topical use. The carnosine-magnesium complex can be absorbed through the skin and may have among others the effect of improving an athlete's physical performance. Further, several diseases where a drop in pH, or pathological oxidation occurs may be improved.

BACKGROUND ART

Carnosine (β-alanyl-L-histidine) is a naturally-occurring histidine-containing compound found in many animal tissues, including skeletal muscle, which is the most abundant source. Carnosine is a multifunctional dipeptide with a molecular weight of 226.23 Da. It is very hydrophilic having a partition coefficient (log P) of −2.972±0.436 (SciFinder-Scholar: Advanced Chemistry Development (ACD/labs) Software v8.14 for Solaris, TM 2007).

The molecular structure of carnosine is shown below:

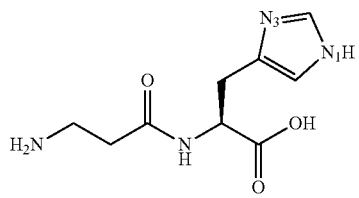

It is a polydentate ligand having several potential binding sites: two imidazole nitrogen atoms, one carboxylic acid group and one amino group.

It is able to form metal complexes with a variety of metal ions, for example, with $Ni^{2+}$, $Mn^{2+}$, $Cd^{2+}$, $Ca^{2+}$, $Sr^{2+}$ and $Mg^{2+}$.

In order to form a complex with $Mg^{2+}$, the carnosine is placed in aqueous solution where the carboxylic function of carnosine is deprotonated (pK=2.6) (E. J. Baran, *Biochemistry*, 2000, 65, 7, 789-797) to form a negatively charged anionic species:

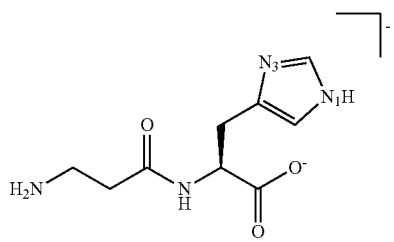

In the presence of a magnesium salt, coordination with magnesium occurs via interaction of the carboxylic function and the $N_1$ nitrogen of the imidazole ring to form a 1:1 cationic carnosine-magnesium complex with a stability constant of the order of 103 (E. J. Baran, Metal Complexes of Carnosine, *Biochemistry*, 2000, 65, 7, 789-797; G. R. Lenz and A. E. Martell, *Biochemistry*, 1964, 3, 750-753):

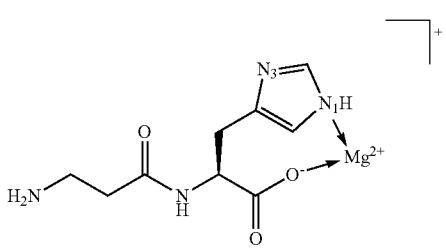

Carnosine is a constituent of several tissues and has numerous biological roles. For example, carnosine is used in enzyme regulation and sarcoplasmic reticulum calcium regulation (G. Begum, et al., *Journal of Sport Nutrition and Exercise Metabolism*, 2005, 15, 493-514). It is also able to act as a pH buffer and as an antioxidant.

Carnosine is broken down in the body by the enzyme carnosinase found in most tissues except skeletal muscle. This partially accounts for the high concentrations of carnosine found in skeletal muscle.

The concentration of carnosine in human skeletal muscle generally ranges from between 5 to 10 mM (wet weight) or from between 15 to 40 mmol/kg (dry weight). Concentrations differ from one animal species to another, partly due to the differences in muscle mass. For example, horses have been reported to have higher carnosine concentrations than greyhound dogs.

Carnosine levels are typically higher in fast-twitch muscle fibres compared to slow-twitch muscle fibres, which is in line with the observation that animals that frequently sprint, have explosive flight reactions, or undergo prolonged hypoxic dives, have higher initial carnosine concentrations.

Human athletes involved in anaerobic sports such as sprinters and bodybuilders were also found to have higher intramuscular concentrations of carnosine. Exercise training was reported to increase muscle carnosine concentrations in these types of athletes as observed by Goebel et al. for six male subjects that performed sprint training twice a week for a total of 16 training sessions. Muscle samples were collected from the vastus lateralis one week before training and again two days following the training protocol. Results revealed that muscle carnosine content and mean power output significantly increased after the eight weeks of training (A. S. B. Goebel et al., *Skin Pharmacology and Physiology*, 2012, 25: 281-287). Carnosine was first discovered as an intracellular pH buffer in 1953 by Severin and colleagues using frog muscle tissue (S. E. Severin, Effect of carnosine and anserine on action of isolated frog muscles—article in Russian—Dokl Akad Nauk SSSR 91: 691-694, 1953). Subsequent studies examining this relationship in human muscle tissue followed thereafter.

When skeletal muscles are involved in moderate to intense exercise, lactic acid is normally generated. This subsequently dissociates into lactate and $H^+$. The production of protons can alter pH levels and it is known that the majority of protons produced in the blood during exercise are buffered by the bicarbonate buffering system. The pKa of this system is 6.1, which is less than that of carnosine (pKa of 6.83), and thus a greater pH change is needed to elicit benefits from this system. Since the pKa of carnosine is closer to the physiological pH, it is likely that this molecule acts as a primary buffer during high-intensity exercise. In fact, the imidazole group of the histidine moiety of carnosine makes it especially effective as a buffer, having a pKa value close to the intracellular pH, as one of the nitrogen atoms of the imidazole ring can be used to accept a proton (A. A. Boldyrev et al., *Physiol Rev* 93, 1803-1845, 2013).

A study conducted by Sewell and associates (D. A. Sewell et al., *Equine Exercise Physiol* 3, 276-280, 1991) specifically examined the buffering capability of carnosine in different horse fibre types. It was found that carnosine contributed to about 20% of the buffering in type I fibres and up to 46% in type IIb fibres. These findings are consistent with the observation that less lactic acid is accumulated in type I fibres due to the lower intensity muscle activity associated with this fibre type.

Aside from buffering effects, carnosine has been found to have other physiological roles. For example, it is able to act as an effective antioxidant against oxidative stress. During exercise, reactive oxygen species (ROS) may be produced due to increased respiration (causing an increase in electron flow in the electron transport system), or due to a decrease in pH (leading to oxygen being released from hemoglobin resulting in increased pO2 in the tissues). Some believe that the production of ROS is related to muscle fatigue during activity. Carnosine is also linked to enzyme regulation related to activation of myosin ATPase, which is used to help maintain ATP stores.

Finally, carnosine has been found to play a role in electron contraction (E-C) coupling in skeletal muscle. An early study by Lamont and Miller (C. Lamont et al., *J Physiol* 454, 421-434, 1992) showed that the presence of 15 mM of carnosine resulted in a significant increase in $Ca^{2+}$ sensitivity in the muscle fibres of *Rana Temporaria*. More recently, Dutka and Lamb (T. L. Dutka et al., *J Muscle Res Cell Motil*, 25, 203-213, 2004) examined whether carnosine affects E-C coupling in functional fibres under physiological conditions. They used mechanically skinned rat extensor digitorum longus muscle fibres. Their results showed that carnosine did not affect $Ca^{2+}$ release from the sarcoplasmic reticulum; however, carnosine was able to increase the $Ca^{2+}$ sensitivity of the contractile components of the muscle fibres. It was suggested that an increase in $Ca^{2+}$ sensitivity could help maintain force production in the later stages of fatigue once $Ca^{2+}$ release begins to decrease. Therefore, higher levels of carnosine can help offset the decrease in $Ca^{2+}$ as well as the accumulation of $H^+$ ions during high-intensity exercise.

Considering that carnosine assists in controlling $Ca^{2+}$ and lactic acid concentrations, acting in addition as an effective antioxidant against oxidative stress, the formulation of a topical product that increases the concentration of carnosine in the body would be of remarkable cosmetic and pharmaceutical interest.

It is well understood that in order for a medicament to function, the active ingredient contained in the medicament must be delivered to the specific site of action in an effective concentration and at the right time. Although these requirements apply to all types of active ingredients, they are particularly important in dermo-cosmetic science for active ingredients having topical functionality (J. W. Wiechers; Skin Delivery: What It Is and Why We Need It; Science and Applications of Skin Delivery Systems; 2008).

An active ingredient that is topically applied to the skin must be able to penetrate the uppermost barrier of the skin, the Stratum Corneum (SC), before being delivered to its site of action in the necessary concentrations. However, aside from specific transport mechanisms, in general, due to the lipophilic properties of the SC, hydrophilic molecules are not able to penetrate the Stratum Corneum effectively.

Therefore, obtaining skin bioavailability of hydrophilic active substances, like peptides or peptide-like substances is challenging (A. S. B. Goebel et al. *Skin Pharmacol Physiol* 2012, 25, 281-287).

Enhancer molecules such as 1,2-pentylene glycol (PG) or ethoxydiglycol may increase the dermal penetration of peptides improving their bioavailability. In fact, it was reported that the addition of PG to a preparation containing L-carnosine or N-acetyl-L-carnosine resulted in a significant increase of the substance within the SC (A. S. B. Goebel et al., *Skin Pharmacology and Physiology*, 2012, 25: 281-287). Approximately 6-fold and higher dipeptide concentrations in the SC and in the viable skin layers were detected compared to the formulation without the enhancer molecule.

Despite some progress, there exists a need in the art for a topical formulation that is able to increase the concentration of carnosine in the body.

SUMMARY OF THE INVENTION

The present inventors have unexpectedly found that the presence of magnesium ions ($Mg^{2+}$) coordinated to carnosine, produces a significant increase in the carnosine level in the lower skin layer following application to the skin. Furthermore, it was found that a composition containing a physiologically active amount of a carnosine-magnesium complex applied to the skin of athletes, considerably improved the physical performance of the athletes.

One aspect of the present disclosure, therefore, concerns a topical composition comprising a physiologically active amount of a carnosine-magnesium complex. The topical composition may be in the form of a gel, a cream, a solution, an ointment, a paste, a lotion, a patch, a spray or a foam. Preferably the topical composition is in the form of a gel. The topical composition may comprise additives selected from the group comprising a lubricant, a carrier, a thickening agent, a preservative, a surfactant, a moisturizing and an emollient agent. It may also comprise a warming agent.

Also the subject of the present disclosure is the use of a topical composition comprising a physiologically active amount of a carnosine-magnesium complex for improving an athlete's physical performance.

The present disclosure also relates to a carnosine-magnesium complex for use in the treatment, amelioration and/or prevention of a number of medical conditions, such as diabetes, metabolic syndrome, cognitive impairment in schizophrenia, autistic spectrum disorders, rheumatoid arthritis, fibromyalgia, dementia, such as Alzheimer's disease, aging, cancer and cardiovascular diseases. cognitive impairments such as those seen schizophrenia, autistic spectrum disorders, dementias including Alzheimer's disease, rheumatoid arthritis, aging, fibromyalgia cancer and cardiovascular diseases.

Further contemplated in the present disclosure is a method of producing a carnosine-magnesium complex.

DETAILED DESCRIPTION OF THE INVENTION

The present disclosure relates to a gel product containing a physiologically active amount of a carnosine-magnesium complex, which can be absorbed by the body through application to the skin and may have the effect of improving an athlete's physical performance. In other words, by forming a complex with magnesium, carnosine may be delivered through the skin and may reach its site of action, such as skeletal muscle tissue or the like. In addition, the carnosine-magnesium complex may act as a buffer agent, in particular as an intracellular and/or interstitial buffer, capable of buffering the pH and/or capable of preventing the accumulation of $H^+$.

Specifically, the present disclosure relates to a topical composition comprising a physiologically active amount of a carnosine-magnesium complex. The topical composition may be in the form of a gel, a cream, a solution, an ointment, a paste, a lotion, a patch, a spray or a foam or in any other form that is suitable for application to the skin. Preferably the topical composition is in the form of a gel.

The term "physiologically active amount", as used herein, may in particular denote an amount of an active ingredient, such as carnosine or a carnosine-magnesium complex, that will elicit the biological or medical response that is sought by the user.

The carnosine-magnesium complex may be present in the topical composition in a quantity ranging from between 0.5 to 5 wt % of the topical composition, which may represent a physiologically active amount of the carnosine-magnesium complex. In particular the carnosine-magnesium complex may be present in the topical composition in a quantity ranging from between 0.6 to 4.5 wt %, in particular 0.7 to 4 wt %, in particular 0.75 to 3.5 wt %, in particular 0.8 to 3 wt %, such as 0.85 to 2.84 wt %, of the topical composition.

In one embodiment the topical composition may comprise a skin absorbing enhancer component. The skin absorbing enhancer may also be referred to as a carrier, in particular as carrier for the carnosine-magnesium complex, which may facilitate the transport of the carnosine-magnesium complex through the skin.

The skin absorbing agent or carrier may in particular comprise an ether alcohol, an aliphatic alcohol or ester or mixtures thereof, in particular an ether alcohol or a mixture of ether alcohols. In particular, the carrier may comprise one or more compounds selected from the group consisting of 2-(2-ethoxyethoxy)ethanol, 3-(3-propoxypropoxy)-1-propanol, 2-(2-propoxyethoxy)ethanol, 1-(1-methyl-2-propoxyethoxy)propan-2-ol, 1-(2-ethoxypropxy)-2-propanol, 1,2-pentylene glycol, propylene glycol, short and long alcohol chain such as ethyl, propyl, isopropyl, myristyl, lauryl and octyl alcohols and esters, such as octyl salicylate and isopropyl myristate. Preferably the skin absorbing agent or carrier may in particular comprise 2-(2-ethoxyethoxy)ethanol, also referred to as ethoxydiglycol. The skin absorbing component may be present in the topical composition in a quantity ranging from between 0.5 to 4 wt %, in particular 0.75 to 3.5 wt %, such as 1.0 to 3 wt %, of the topical composition. In a further embodiment the topical composition may comprise one or more components selected from the group comprising a lubricant, a carrier, a thickening agent, a preservative, a surfactant, water, a moisturizing agent and an emollient agent.

Lubricants may be selected from the group comprising silicon oils, propyl-eptyl-caprylate, dicaprylil-carbonate, dicaprylil ether, ethylesylcocoate, isopropylmiristate, exyllaurate, dibuthyladipate and isopropyladipate, and mixtures thereof.

A lubricant may be present in the topical composition in a quantity ranging from between 1 to 20 wt % of the topical composition.

Carriers may be selected from the group comprising silicon dioxide, titanium dioxide, zinc oxide and acrylate copolymers and mixtures thereof. A carrier may be present in the topical composition in a quantity ranging from between 0.2 to 6 wt % of the topical composition, preferably in a quantity ranging from between 0.4 to 0.2 wt % of the topical composition.

A thickening agent may be selected from the group comprising sclerotium gum, xantan gum, guar gum, pectine, agar agar, ethoxy ethyl cellulose, hydroxyl ethyl cellulose, hydroxyl propyl cellulose, hydroxyl propylmethyl cellulose, hyaluronic acids, and mixtures thereof.

A thickening agent may be present in the topical composition in a quantity ranging from between 0.1 to 4 wt % of the topical composition, preferably in a quantity ranging from between 0.2. to 2 wt % of the topical composition.

A preservative may be selected from the group comprising phenoxyethanol, ethylhexylglycerine, benzoic acid, benzoic salts, benzoic esters, sorbic acid and sorbic salts, dehydroacetic acid and dehydroacetic salts, and mixtures thereof.

A preservative may be present in the topical composition in a quantity ranging from between 0.1 to 1.5 wt % of the topical composition, preferably in a quantity ranging from between 0.4 to 0.8 wt % of the topical composition.

A surfactant may be selected from the group comprising cationic surfactants such as quaternary ammonium salts, anionic surfactants such as sodium laurylsulphate, non-ionic surfactants such as alkylpolyglucoside or amphoteric surfactants such as cocamidopropylbetaine.

A surfactant may be present in the topical composition in a quantity ranging from between 0.05 to 2 wt % of the topical composition, preferably in a quantity ranging from between 0.1 to 1 wt % of the topical composition.

A moisturing agent may be selected from the group comprising glycerin, penthylene glycol, hyaluronic acid, trehalose, lynositol and mixtures thereof.

A moisturizing agent may be present in the topical composition in a quantity ranging from between 0.5 to 5 wt % of the topical composition, preferably in a quantity ranging from between 1 to 3 wt % of the topical composition.

An emollient may be selected from the group comprising sweet almond oil, aloe vera, butyrospermum parkii butter olea europea oil, argan oil, persea gratissima oil, coconut oil and mixtures thereof.

An emollient may be present in the topical composition in a quantity ranging from between 1 to 10 wt % of the topical composition, preferably in a quantity ranging from between 2 to 4 wt % of the topical composition.

Water may be present in the topical composition in a quantity ranging from between 60 to 95 wt % of the topical composition, preferably in a quantity ranging from between 80 to 95 wt % of the topical composition.

The topical composition of the present disclosure can be modified by introducing a component that has the effect of warming up the skin during application. This component is referred to as a warming agent.

The topical composition of the present disclosure may therefore comprise a warming agent. The warming agent may be chosen from any suitable warming agent known in the art. Examples of warming agents that may be employed in the topical composition of the present disclosure include warming agents selected from the group comprising methyl nicotinate, ethyl nicotinate, hexyl nicotinate, benzyl nicotinate, tocopheryl nicotinate, *Capsicum annuum* oleoresin, *Cinnamomum camphora* bark oil, methyl salicylate, and mixtures thereof.

In one embodiment of the present disclosure, a nicotinate may be present in the topical composition in an amount of between 0.05-0.1 wt % of the topical composition.

In another embodiment of the present disclosure, *Capsicum annuum* oleoresin may be present in the topical composition in an amount of between 0.5-1 wt % of the topical composition.

In a further embodiment of the present disclosure, *Cinnamomum camphora* bark oil may be present in the topical composition in an amount from 1-10 wt % of the topical composition.

In another embodiment, methyl salicylate may be present in the topical composition in an amount from 1-10 wt % of the topical composition. In an embodiment, the topical composition may further comprise creatine and/or carnitine, in particular a creatine-magnesium complex and/or a carnitine-magnesium complex. In other words, the topical composition may comprise a combination of a carnosine-magnesium complex with a creatine-magnesium complex and/or a carnitine-magnesium complex, which may provide for a particular pronounced effect, or even synergistic effect, of improving an athlete's physical performance. Creatine may act as an extracellular buffer, if paired with carnosine has a synergistic effect and improves athletic performance by providing both intracellular and extracellular buffers. Carnitine could synergize with carnosine via its role in energy production as well as treatment of autistic spectrum disorders.

In an embodiment, the topical composition may further comprise sodium bicarbonate, which may buffer the highly acidic L-carnitine L-tartrate and confer additional benefit as an extracellular buffer. In particular, sodium bicarbonate may serve as an extracellular buffer when paired with carnosine would be improved by carnosine's ability to mitigate hydrogen, this extracellular nonbicarbonate buffering would improve sodium bicarbonate efficacy by mitigating the release of H+ ions coming from the back-titration of the nonbicarbonate buffers.

In an embodiment, the topical composition may further comprise 5-hydroxytryptophan (5-HTP) also known as oxitriptan. 5-HTP is a naturally occurring amino acid and chemical precursor as well as a metabolic intermediate in the biosynthesis of the neurotransmitters serotonin. Carnosine a known cytoplasmic neuropeptide thus could aid in the delivery of 5-HTP topically.

In an embodiment, the topical composition may further comprise potassium in forms including but not limited to potassium citrate or potassium bicarbonate. Such a formulation could help in delaying a drop in interstitial pH during moderate to intense exercise. The improvement in extracellualar pH environment could improve the K+ balance and prevent a drop in blood flow during the onset of fatigue.

In an embodiment, the topical composition may further comprise D-ribose. D-ribose has been shown to increase cellular energy synthesis in heart and skeletal muscle, with the addition of carnosine could be used to impact fibromyalgia and chronic fatigue syndrome.

In an embodiment, the topical composition may further comprise Coenzyme Q10 (CoQ10). CoQ10 is an essential electron carrier in the mitochondrial respiratory chain, is a strong antioxidant and it alters mitochondrial function. Its deficiency leads to increased reactive oxygen species (ROS) generation. It has been shown that CoQ10 is deficient in mononuclear cells in fibromyalgia patients. CoQ10 is lipophilic, as such there are existing topical formulations, however the antioxidant combination of CoQ10 and Carnosine that penetrates the skin has never been possible due to carnosine being hydrophilic. This combination could be effective at reducing free radicals to treat conditions like fibromyalgia.

An exemplary composition of the topical composition provided as a gel is given by the following ingredients (in percentage by weight):

| Ingredient | Concentration |
| --- | --- |
| Water | Balance |
| Glycerine | 2.20%-4.10% |
| Ethoxydiglycol | 0.81%-3.15% |
| Carnosine-magnesium complex | 0.85%-2.84% |
| PVP | 0.76%-1.87% |
| Hydroxypropyl cellulose | 0.72%-1.82% |
| Phenoxyethanol | 0.12%-1.43% |

The topical composition comprising a carnosine-magnesium complex may bypass hydrolysis by carnosinase and may serve as a pH buffer.

The carnosine-magnesium complex of the present disclosure can be prepared by combining a magnesium salt, an aqueous solution, and carnosine. Preferably the magnesium salt is added to the aqueous solution containing carnosine. Preferably a stoichiometric amount of a magnesium salt is used.

Suitable magnesium salts include magnesium sulphate or magnesium chloride or magnesium citrate or magnesium lactate. Preferably, the magnesium salt is magnesium sulphate. Preferably the aqueous solution is water.

The concentration of the magnesium salt in the aqueous solution is in the range between 1 and 10% by weight, preferably in the range between 1 and 5% by weight.

The concentration of the carnosine in the aqueous solution is in the range between 1 and 10% by weight, preferably in the range between 1 and 5% by weight.

Once the carnosine and the magnesium salt are in contact with each other in an aqueous solution at room temperature, the carnosine-magnesium complex form almost instantaneously.

Once formed, the carnosine-magnesium complex can be used to prepare a topical composition. The topical composition may be prepared by stirring the different components.

The carnosine-magnesium complex can be used to increase the concentration of carnosine in the lower skin layers. Such skin layers include for example the epidermidis.

The carnosine-magnesium complex of the present disclosure may be used to increase the athletic performance of a subject such as effort duration, speed and muscles recovery.

The carnosine-magnesium complex of the present disclosure may be used in the treatment, amelioration and/or prevention of a number of medical conditions, such as diabetes, metabolic syndrome, cognitive impairment in schizophrenia, autistic spectrum disorders, rheumatoid arthritis, fibromyalgia, dementia, such as Alzheimer's disease, aging, cancer and cardiovascular diseases. The carnosine-magnesium complex of the present disclosure may improve many medical conditions, in particular where a drop in pH or a pathological oxidation occurs.

Also the subject of the present disclosure is the use of a topical composition comprising a carnosine-magnesium complex for increasing the concentration of carnosine in the lower skin layers, such as the epidermidis.

The topical composition of the present disclosure may also be used to increase the athletic (physical) performance of a subject.

Also the subject of the present disclosure is a carnosine-magnesium complex as described herein for use in the treatment, amelioration and/or prevention of a medical condition selected from the group consisting of diabetes, metabolic syndrome, cognitive impairment in schizophrenia, autistic spectrum disorders, rheumatoid arthritis, fibromyalgia, dementia, such as Alzheimer's disease, aging, cancer and cardiovascular diseases.

Diabetes and metabolic syndrome: The destructive changes in vital enzymes and other proteins by glucose (the glycation process) is one of the major causes of aging and diabetes. This process is accelerated in diabetes due to constantly elevated glucose levels. A substance that can prevent glycation in the first place, or one that can reverse existing protein glycation, may therefore be a powerful therapeutic agent in the treatment of diabetes. Carnosine may stabilize red blood cell membranes against the damaging effects of glycation products in diabetes. Additionally, it protects human LDL cholesterol from both oxidation and glycation. The topical composition as described herein may thus be used for treating Diabetes. The recommended dosage is 4-6 ml of the exemplary composition of the topical composition illustrated above four times a day applied to all four limbs.

Improved Cognition In Schizophrenia: Targeting glutamatergic dysfunction provides an exciting opportunity to improve cognitive impairment in schizophrenia. One treatment approach has targeted inadequate antioxidant defenses at glutamatergic synapses. Animal and human data suggest NMDA antagonists worsen executive cognitive controls, e.g. increase perseverative responses and impair set-shifting. We conducted a preliminary study to test the hypothesis that L-carnosine, an antioxidant and anti-glycation agent which is co-localized and released with glutamate would improve executive dysfunction, a cognitive domain associated with glutamate. Seventy-five symptomatically stable adults with chronic schizophrenia were randomly assigned to L-carnosine as adjunctive treatment (2 g/day) or a matched placebo in a double-blind manner for 3 months. On the strategic target detection test, the L-carnosine group displayed significantly improved strategic efficiency and made fewer perseverative errors compared with placebo. The recommended dosage is 4-6 ml of the exemplary composition of the topical composition illustrated above four times a day applied to all four limbs.

Autistic Spectrum Disorders: The Childhood Autism Rating Scale, the Gilliam Autism Rating Scale, the Expressive and Receptive One-Word Picture Vocabulary tests, and Clinical Global Impressions of Change were measured. Children on placebo did not show statistically significant changes. After 8 weeks on L-carnosine, children showed statistically significant improvements on the Gilliam Autism Rating Scale (total score and the Behavior, Socialization, and Communication subscales) and the Receptive One-Word Picture Vocabulary test (all P<0.05). Improved trends were noted on other outcome measures. The recommended dosage is 4-6 ml of the exemplary composition of the topical composition illustrated above four times a day applied to all four limbs.

Rheumatoid Arthritis: The therapeutic potential of Carnosine for use in the treatment of rheumatoid arthritis (RA) has been investigated both in vitro and in vivo with great success. Suppression of intracellular oxidant levels was observed along with systemic anti-inflammatory activity that protected the joints from oxidative stress and halted further degradation. Carnosine's anti-inflammatory potential in autoimmune diseases is just beginning to be realized in such studies. The only limit to this novel treatment method is the oral delivery of carnosine, there is a large non-responder rate to oral carnosine ingestion. The topical composition according to the present disclosure overcomes such limitations and therefore has a therapeutic potential for treating rheumatoid arthritis. The recommended dosage is 4-6 ml of the exemplary composition of the topical composition illustrated above four times a day applied to all four limbs.

Fibromyalgia: Oxidative stress is associated with the symptoms of fatigue in fibromyalgia. The ability of topical composition according to the present disclosure to mitigate oxidative stress has great potential to address the symptoms and/or progression of fibromyalgia. The recommended dosage is 4-6 ml of the exemplary composition of the topical composition illustrated above four times a day applied to all four limbs.

Dementia, including but not limited to Alzheimer's Disease (AD): Carnosine can suppress amyloid-beta peptide toxicity, inhibit production of oxygen free-radicals, scavenge hydroxyl radicals and reactive aldehydes, and suppresses protein glycation. Glycated protein accumulates in the cerebrospinal fluid (CSF) of AD patients. Homocarnosine levels in human CSF dramatically decline with age. CSF composition and turnover is controlled by the choroid plexus which possesses a specific transporter for carnosine and homocarnosine. Carnosine reacts with protein carbonyls and suppress the reactivity of glycated proteins. Carbonic anhydrase (CA) activity is diminished in AD patient brains. Administration of CA activators improves learning in animals. Carnosine is a CA activator. Protein cross-links are present in neurofibrillary tangles in AD brain. Carnosine stimulates proteolysis in cultured myocytes and senescent cultured fibroblasts. These observations suggest that carnosine and related structures should be explored for therapeutic potential towards AD and other neurodegenerative disorders. The recommended dosage is 4-6 ml of the exemplary composition of the topical composition illustrated above four times a day applied to all four limbs.

Anti-aging: Aging is a physiological process whose precise underlying mechanisms are unclear, although it may include DNA damage and telomere shortening, changes in gene expression, induction of oxidative stress, impairment of ATP synthesis, and accumulation of altered proteins. Many physiological effects observed in experimental studies with cell culture, animals and humans are assigned to carnosine. In this scenario, carnosine is thought to counteract several mechanisms associated to aging process due to its presumable biochemical properties, including antioxidant, bivalent metal ion chelating, muscular proton buffering, anti cross-linking, and reactive carbonyl scavenger activities Homocarnosine levels in human CSF dramatically decline with age. The topical composition according to the present disclosure is effective for delivering carnosine. It has potential to compensate for the natural reduction in carnosine levels due to aging. Recent research suggests that carnosine can make an important contribution in the aging related reduction in telomere shortening rate and damages in telomeric DNA. The recommended dosage is 4-6 ml of the exemplary composition of the topical composition illustrated above four times a day applied to all four limbs.

Cancer: As an antioxidant, carnosine helps block the DNA damage that can lead to cancerous transformation in cultured cells and it increases the life span of cells cultured from young subjects in the laboratory. Carnosine also prevents release of inflammatory cytokines in intestinal cells, reducing a significant risk for colon cancers. Its ability to inhibit new metastases, and to interfere with cancer cells' energy metabolism, make it still more appealing as a potential anticancer nutrient. The recommended dosage is 4-6 ml of the exemplary composition of the topical composition illustrated above four times a day applied to affected area and all four limbs.

Cardiovascular diseases: Carnosine protects against ischemia/reperfusion injury in a number of remarkable ways. It protects brain cells after a stroke by reducing toxicity of the excitatory neurotransmitter glutamate.

Interestingly, treatment with carnosine significantly reduced the amount of brain tissue involved in experimentally-produced strokes in mice. Perhaps more impressively, carnosine supplements protect animals' brains against localized ischemia in the first place. This discovery has been credited with increasing survival of experimental animals following stroke. The recommended dosage is 4-6 ml of the exemplary composition of the topical composition illustrated above four times a day applied to all four limbs.

The topical composition of the present disclosure is for application to the skin. It may be applied to skin anywhere on the body, but is most suitable to be applied to the legs, arms, torso.

When the topical composition comprising a carnosine-magnesium complex is applied to the skin, after 24 hours between 0.0033% and 0.02% of the carnosine applied to the skin may pass the skin layer of a EpiDerm™ reconstructed human epidermis model and may be found in the medium.

When the topical composition comprising a carnosine-magnesium complex is applied to the skin, after 48 hours between 0.005% and 0.01% of the carnosine applied to the skin may pass the skin layer of a EpiDerm™ reconstructed human epidermis model and may be found in the medium.

When the topical composition comprising a carnosine-magnesium complex is applied to the skin, after 24 hours between 0.033% and 0.01% of the carnosine applied to the skin may be found in the homogenates of the skin model of EpiDerm™ reconstructed human epidermis model.

When the topical composition comprising a carnosine-magnesium complex is applied to the skin, after 48 hours between 0.05% and 0.07% of the carnosine applied to the skin may be found in the homogenates of the skin model of EpiDerm™ reconstructed human epidermis model.

The multiple layers of the topical composition may be applied to an area of skin. Preferably between 1 and 5 coats of the topical composition are applied to an area of skin, more preferably between 1 and 3 coats of the topical composition are applied to an area of skin.

The one or more coats of topical composition may be applied to the skin from between 1 to 5 times a day, preferably from between 1 to 3 times a day. The topical composition may be applied to the skin at any time of day and before, after, or during exercise. Preferably the topical composition is applied to the skin before and after exercise.

The topical composition may be applied to the skin at any time of year and at any ambient temperature.

The topical composition of the present disclosure may be used as needed for as long as required.

The topical composition of the present disclosure may be used by adult subjects of all sex, and ethnicity.

EXPERIMENTAL SECTION

Materials and Methods

The following three samples were used in the experiments:

Sample A: Carnosine-magnesium complex in the final gel formulation (having the formulation set out below in Table 1):

TABLE 1

| Carnosine-magnesium gel formulation | |
|---|---|
| Component | Quantity (g) |
| Water | 90.260 |
| Glycerine | 3.000 |
| Carnosine | 1.500 |
| Magnesium Sulphate | 1.640 |
| 2-(2-Ethoxyethoxy)ethanol | 2.000 |
| Sclerotium Gum | 0.800 |
| Phenoxyetnanol, Ethylhexylglycerine | 0.800 |
| TOTAL | 100.000 |

Sample B: Free carnosine, in the final gel formulation as for sample A.

Sample C: Final gel formulation but without the active ingredient carnosine All the samples are gel formulations.

Example 1

Evaluation of the Transepidermal Penetration of the Carnosine-Magnesium Complex in Gel Formulation in 3D-Skin Models The focus of the described experiments is to investigate the delivery of L-carnosine to human skin by the gel formulation containing L-carnosine in association with magnesium, which forms a mono-cationic complex (carnosine-magnesium complex), with the aim of improving bioavailability. The investigation was conducted using a carnosine-free preparation as the reference product (S. E. Severin et al. Effect of carnosine and anserine on action of isolated frog muscles (article in Russian). *Dokl Akad Nauk SSSR* 91: 691-694, 1953).

EpiDerm™ Reconstructed Human Epidermis (RHE) Model and Treatments

Reconstructed human epidermis (RHE) was used as a human skin tissue model. EpiDerm™ Tissue Model was purchased from MatTek (MatTek In Vitro Life Science Laboratories, Bratislava, Slovak Republic). Upon reception, tissues were transferred into SkinEthic™ Maintenance Medium and kept at 37° C. in a humidified 5% $CO_2$ atmosphere. EpiDerm™ Reconstructed Human Epidermis (RHE) model consists of a three-dimensional epidermal tissue grown at the air liquid interface from normal human keratinocytes. The model is histologically similar to human epidermis, having all differentiated cellular layers, and a functional permeability barrier.

Before carrying out the treatments, the medium was withdrawn and fresh medium was added. For the treatments, 10 μL of the three different mixtures (A: carnosine-complex; B: free carnosine without the enhancer; C: vehicle) were each topically applied over separate RHE tissues either in a single dose for 24 h or in a repeated application every 24 h for a total of 48 h. The control tissue was only exposed to the medium. Since no differences between doses applied at 24 and 48 h were observed for the control tissues, the samples were pooled and presented as the control group. All mixtures and control samples were assayed in triplicate by using three sets of RHE for each group.

After 24 or 48 h of treatment, tissue medium aliquots were collected and centrifuged for 20 minutes to remove insoluble impurities and tissue debris at 1000×g at 4° C. The clear supernatants were stored at −20° C. until analysis. After washing with PBS and snap-freezing in liquid nitrogen, the RHE tissues were homogenized in a glass potter with 150 μl of PBS on ice. The homogenates were then centrifuged for 5 minutes at 5000×g to obtain the supernatants that were stored at −20° C. until analysis.

ELISA for Carnosine

Carnosine levels were determined in the RHE culture media and homogenates collected at different time points (24 or 48 h), using an ELISA (enzyme-linked immunosorbent assay) kit (Elabscience Biotechnology Co., Ltd). The procedure was performed according to the manufacturer's instructions. The optical absorbance was measured with a microplate reader at 450 nm. A calibration curve was obtained using carnosine as a standard. All the samples were assayed in duplicate. The lower limit of detection for carnosine was 8.438 ng/mL. Results are expressed as ng/mL. Changes in carnosine levels from the baseline level (control RHE) were compared on the basis of a Student's t-test. A P-value of <0.05 was considered significant.

Results

The carnosine levels were measured in media and homogenates and results for the three samples, A, B and C at 24 hours (first time point) and 48 hours (second time point) are reported below.

Carnosine Levels in Media

At the first time point, after 24 hours from the treatment, the highest level of carnosine was detected for sample A with a P-value of 0.028 compared to the carnosine level in the control tissue. Even if the carnosine level for sample B was higher than of the control tissue, this data had a non-significant P-value (p=0.065).

The comparison between samples A and B shows that the carnosine level detected in the medium of the sample A was significantly higher than the carnosine level detected in the medium of the sample B (p=0.043). The carnosine level detected in the medium of sample C was comparable to the concentration of carnosine recorded for the control tissue.

At the second time point, after 48 hours from the treatment, the carnosine level in the medium of sample A was lower than the level detected at the first time point, although it was greater than the carnosine level detected in the control tissue.

The carnosine levels in the medium of samples B and C were similar to the levels detected at the first time point.

TABLE 2 detection values of carnosine in media

| | Sample | ng/ml | S.D |
|---|---|---|---|
| | Control (CTRL) | 6.2 | 3.8 |
| 1st time point (24 h) | A24 | 19.3 | 3.4 |
| | B24 | 12.9 | 1.6 |
| | C24 | 7.1 | 1.7 |
| 2nd time Point (48 h) | A48 | 14.6 | 2.7 |
| | B48 | 12.5 | 6.8 |
| | C48 | 6.7 | 5.0 |

TABLE 3 p-values of carnosine in media

| | p-value |
|---|---|
| CTRL vs A24 | 0.028 |
| CTRL vs B24 | 0.065 |
| CTRL vs C24 | 0.712 |
| CTRL vs A48 | 0.062 |
| CTRL vs B48 | 0.336 |
| CTRL vs C48 | 0.911 |
| A24 vs B24 | 0.043 |

TABLE 3-continued p-values of carnosine in media

| | p-value |
|---|---|
| A48 vs B48 | 0.648 |
| A24 vs A48 | 0.133 |

Carnosine Levels in RHE Lysates

At the first time point, the tissue treated with sample A had a carnosine content significantly lower than the level detected in the control tissue (p=0.019).

In the tissue treated with sample B, the carnosine level increased as compared to the control tissue, but this data was non-significant (p=0.708).

The carnosine level detected in the tissue treated with sample C was similar to that of the control.

After 48 hours, at the second time point, the carnosine levels detected were equivalent to the tissue control for all the samples.

TABLE 4 detection values of carnosine in homogenates

| | Sample | ng/ml | S.D |
|---|---|---|---|
| | Control (CTRL) | 107.8 | 11.2 |
| 1st time point (24 h) | A24 | 65.9 | 9.4 |
| | B24 | 127.0 | 14.5 |
| | C24 | 98.3 | 9.0 |
| 2nd time point (48 h) | A48 | 98.0 | 8.1 |
| | B48 | 99.0 | 27.8 |
| | C48 | 105.6 | 7.3 |

TABLE 5 p-values of carnosine in homogenates

| | p-value |
|---|---|
| CTRL vs A24 | 0.019 |
| CTRL vs B24 | 0.218 |
| CTRL vs C24 | 0.363 |
| CTRL vs A48 | 0.326 |
| CTRL vs B48 | 0.708 |
| CTRL vs C48 | 0.800 |
| A24 vs B24 | 0.004 |
| A48 vs B48 | 0.956 |
| A24 vs A48 | 0.011 |

Conclusions

According to the data collected, it appears that at the first time point, 24 hours, the preparation A (carnosine-magnesium complex in the final formulation) showed a significant increase in the delivery of carnosine in the lower skin layer. In fact, a higher level of carnosine passed into the medium with respect to preparation B. As counter proof, the content of carnosine was lower in the corresponding tissue.

At the second time point, 48 hours, a non-significant increase in carnosine levels were observed in the medium. This may be due to the limitations of the in vitro RHE model, which after 48 hours loses its initial properties and may therefore be less reliable.

Finally, it can be concluded that the carnosine-magnesium complex was effective in increasing the delivery of carnosine though a 3D skin model.

In fact, the carnosine concentration remaining in the tissues was almost half that of the sample containing free carnosine.

Example 2

Evaluation of the Effects of the Carnosine-Magnesium Gel in Soccer Players. Pilot Study.

The aim of the pilot study was to evaluate, the effects of the carnosine-magnesium complex present in a new gel formulation for topical use on the performances of soccer players.

Methods

The study was divided into two parts corresponding to the following exercises:

1) a yo-yo intermittent recovery test;
2) 1,000 m sprint test repeated 3 times (1' 30 sec between series). Tests were performed for each athlete with and without carnosine-magnesium gel.

Preparation Before the Performance with a Warm-Up Cream Application

A warm-up cream containing capsicum was used to optimize muscle preparation before the tests. This type of warm-up cream is commonly used by sportsmen before any physical activity to prevent injuries and traumas of a muscular nature that may occur during physical activity.

Study Design

The performance of 11 adult athletes between 18 and 35 years (soccer players) was evaluated. For the duration of the test period the athletes did not take any dietary supplement, were not treated with drugs and refrained from additional training or competitions.

During a pre-study stage, the differences between the athlete's performances with and without the warm-up cream were evaluated in order to verify whether the warm-up cream caused any relevant effects.

In the study stage, application of the warm-up cream on the legs was followed by carnosine-magnesium gel topical treatment using sample A. During the study stage the athletes did not perform any other sporting activities or competitions. For each type of exercise, there was a delay of three days between the test performed with application of only the warm-up cream and the test with application of both the warm-up cream and carnosine-magnesium gel (sample A).

Yo-Yo Intermittent Recovery Test

In the yo-yo test, the athlete runs between speed delimiters placed 40 meters apart from each other. Speed is regularly incremented and the test ends when the subject is no longer able to maintain speed. The test result is determined by the distance covered during the test, and it is a resistance test.

1000 Meters×3 Repetitive Test (1 Minute and 30 seconds of Rest Between Each Test)

The time an athlete took to run 1000 m was recorded. The test was repeated three times and the athlete was allowed to rest for 1 minute and thirty seconds between each test. The test measures resistance.

Results

The results of the performance of each individual athlete during the different tests performed without application of any topical cream, after application of the warm-up cream and after application of both the warm-up cream and carnosine-magnesium gel (sample A), are summarized in Tables 6 and 7.

All athletes reported satisfaction and good sensations in their legs during and after exercise. No recognized local or systemic side effects were observed.

TABLE 6

Results for Yo-Yo test 40 m

| Athlete | Without any cream | | Only warm-up cream | | With warm-up cream and carnosine-magnesium gel | | Improvement due to the addition of carnosine-magnesium gel |
|---|---|---|---|---|---|---|---|
| | Travelled distance | Overall rating | Travelled distance | Overall Rating* | Travelled distance | Overall Rating* | |
| A. F. | 1670 m | 16 | 1672 m | 16 | 1690 m | 17 | +1 |
| F. F. | 1701 m | 17 | 1700 m | 17 | 1740 m | 17 | 0 |
| S. A. | 1487 m | 15 | 1490 m | 15 | 1600 m | 16 | +1 |
| C. S. | 1553 m | 15 | 1550 m | 15 | 1680 m | 17 | +2 |
| B. G. | 1420 m | 14 | 1420 m | 14 | 1630 m | 16 | +2 |
| T. A. | 1760 m | 17 | 1760 m | 17 | 1960 m | 20 | +3 |
| B. S. | 1443 m | 15 | 1440 m | 15 | 1480 m | 15 | 0 |
| S. S | 1501 m | 15 | 1500 m | 15 | 1610 m | 16 | +1 |
| A. A. | 1659 m | 16 | 1660 m | 16 | 1690 m | 17 | +1 |
| S. P. | 1780 m | 18 | 1780 m | 18 | 1830 m | 19 | +1 |
| D. S. | 1692 m | 16 | 1690 m | 16 | 1680 m | 16 | 0 |

TABLE 7

Results for 1000 metres × 3 repetitive tests (1 minute and 30 seconds between tests)

| Athlete | A Average time without any cream | B Average time with only warm-up cream | C Average time with warm-up cream and carnosine-magnesium gel | D [1] Improvement due to the addition of carnosine-magnesium gel |
|---|---|---|---|---|
| A. F. | 4', 13 sec | 4', 12 sec | 4', 02 sec | +10 sec |
| F. F. | 4', 09 sec | 4', 09 sec | 3', 57 sec | +12 sec |
| S. A. | 4', 15 sec | 4', 14 sec | 4', 05 sec | +9 sec |
| C. S. | 4', 05 sec | 4', 04 sec | 3', 59 sec | +5 sec |
| B. G. | 4', 29 sec | 4', 28 sec | 4', 22 sec | +6 sec |
| T. A. | 3', 57 sec | 3', 58 sec | 3', 47 sec | +11 sec |
| B. S. | 4', 02 sec | 4', 02 sec | 3', 10 sec | +22 sec |
| S. S. | 4', 16 sec | 4', 16 sec | 4', 07 sec | +9 sec |
| A. A. | 4', 18 sec | 4', 17 sec | 4', 12 sec | +5 sec |
| S. P. | 4', 07 sec | 4', 04 sec | 4', 03 sec | +0.1 sec |
| D. S. | 3', 53 sec | 3', 52 sec | 3', 42 sec | +10 sec |

Note
[1] The numbers in column D correspond to the difference between the values in column B and C. The time reduction is indicated as a positive value.

Conclusions

The in vitro investigation showed that with the application of the carnosine-magnesium gel there was a significant increase in the performance of all the athletes that participated in the study.

Improvements were observed in both the speed endurance and resistance tests.

Athletes did not report any side effects after carnosine-magnesium gel treatment.

The invention claimed is:

1. A topical composition comprising a physiologically active amount of a carnosine-magnesium complex, wherein the physiologically active amount of the carnosine-magnesium complex represents a quantity of the carnosine-magnesium complex of from 0.5 to 5 wt % of the topical composition for delivering carnosine to skeletal muscle tissue.

2. The topical composition according to claim 1, in which the carnosine-magnesium complex has the following formula:

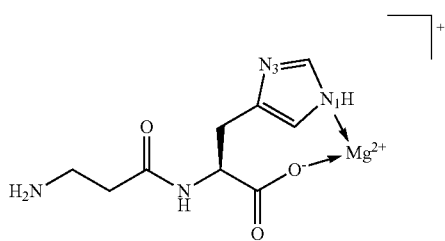

3. The topical composition according to claim 1, wherein the topical composition is in the form of a gel, a cream, a solution, an ointment, a paste, a lotion, a patch, a spray or a foam.

4. The topical composition according to claim 1, further comprising a skin absorbing enhancer component chosen from the group consisting of 1,2-pentylene glycol, ethoxydiglycol, propylene glycol, ethyl, propyl, isopropyl, myristyl, lauryl and octyl alcohols, octyl salicylate and isopropyl miristate.

5. The topical composition according to claim 1, further comprising a lubricant, a carrier, a thickening agent, a preservative, a surfactant, water, a moisturizing agent and an emollient agent.

6. The topical composition according to claim 4, wherein the lubricant is selected from the group consisting of silicon oils, propyl-heptyl-caprylate, dicaprylyl-carbonate, dicaprylyl ether, ethylhexylcocoate, isopropylmyristate, hexyllaurate, dibutyladipate and isopropyladipate, and mixtures thereof; the carrier is selected from the group comprising silicon dioxide, titanium dioxide, zinc oxide, acrylate copolymers and mixtures thereof; the thickening agent is selected from the group comprising sclerotium gum, xantan gum, guar gum, pectine, agar agar, ethoxy ethyl cellulose, hydroxyl ethyl cellulose, hydroxyl propyl cellulose, hydroxyl propylmethyl cellulose, hyaluronic acids, and mixtures thereof; the preservative is selected from the group comprising phenoxyethanol, ethylhexylglycerine, benzoic acid, benzoic salts, benzoic esters, sorbic acid, sorbic salts, dehydroacetic acid, dehydroacetic salts, and mixtures thereof; and the surfactant is selected from the group comprising quaternary ammonium salts, sodium laurylsulphate, alkylpolyglucoside and cocamidopropylbetaine.

7. The topical composition according to claim 1, further comprising a warming agent selected from the group comprising methyl nicotinate, ethyl nicotinate, hexyl nicotinate, benzyl nicotinate, tocopheryl nicotinate, *Capsicum annuum* oleoresin, *Cinnamomum camphora* bark oil, methyl salicylate, and mixtures thereof.

8. The topical composition according to claim 6, wherein if a nicotinate is present in the composition, it is present in 0.05-0.1 wt % of the composition; if *Capsicum annuum* oleoresin is present in the composition, it is present in 0.5-1 wt % of the composition; if *Cinnamomum camphora* bark oil is present in the composition, it is present in 1-10 wt % of the composition; and if methyl salicylate is present in the composition, it is present in 1-10 wt % of the composition.

9. A method of producing the carnosine-magnesium complex of the topical composition according to claim 1, comprising the step of adding a stoichiometric amount of magnesium sulphate or magnesium chloride or magnesium citrate or magnesium lactate to an aqueous solution of carnosine.

* * * * *